United States Patent [19]
King et al.

[11] Patent Number: 5,310,248
[45] Date of Patent: May 10, 1994

[54] AUTOMATIC VEIN IDENTIFYING METHOD AND FOLLOWER APPARATUS FOR USE IN A ROBOT MINING SYSTEM

[75] Inventors: Robert H. King, Conifer; Dale L. Lauer, Golden, both of Colo.

[73] Assignee: Colorado School of Mines, Golden, Colo.

[21] Appl. No.: 712,707

[22] Filed: Jul. 19, 1991

[51] Int. Cl.$^5$ ............... E21C 35/24; G01N 21/25
[52] U.S. Cl. ................... 299/1.1; 356/407; 356/419
[58] Field of Search ............ 299/1.1, 1.2, 30; 356/402, 407, 418, 419, 425

[56] References Cited

U.S. PATENT DOCUMENTS

| | | | |
|---|---|---|---|
| 3,333,893 | 8/1967 | Heimaster | 299/1.2 |
| 4,079,997 | 3/1978 | Bienko et al. | 299/1.2 |
| 4,134,683 | 1/1979 | Goetz et al. | 356/407 |
| 4,192,550 | 3/1980 | Heimaster | 299/1.1 |

FOREIGN PATENT DOCUMENTS

| | | | |
|---|---|---|---|
| 754060 | 8/1980 | U.S.S.R. | 299/1.1 |
| 901514 | 1/1982 | U.S.S.R. | 299/1.1 |

Primary Examiner—David J. Bagnell
Attorney, Agent, or Firm—Sheridan Ross & McIntosh

[57] ABSTRACT

The present apparatus makes use of a novel mineral identification system to not only identify the desired minerals and estimate a percent of mineralization, but also locate their presence on the mining face in an x, y coordinate manner in order to guide the mining operation of the associated robot mining apparatus. This is accomplished through the use of a camera and video monitor system which picks up the light returned from the mining face as illuminated by the light source. Therefore, on a pixel by pixel basis the camera identifies the light intensity returned from the mining face. In order to obtain the unique light signature of the desired minerals, a plurality of narrow band light filters is used to screen the light reflected from the mining face prior to its being focussed on the video camera. Thus, a three dimensional matrix is formed, consisting of data entries for each pixel of the video image for each frequency of interest as determined by the filter used to filter the returned light prior to its focussing onto the video camera.

24 Claims, 9 Drawing Sheets

BOUNDARY PROCESS
SP = STARTING POINT

AUTOMATIC VEIN IDENTIFYING METHOD AND FOLLOWER APPARATUS FOR USE IN A ROBOT MINING SYSTEM

FIELD OF THE INVENTION

This invention relates to automated mining systems and, in particular, to apparatus and a method for controlling the operation of a robot mining system to enable the robot mining system to automatically follow a vein of minerals independent of operator intervention.

PROBLEM

It is a problem in the field of mining to efficiently mine materials in either a hazardous environment or where the vein of mineralization is of small cross sectional area. It is inadvisable to use human miners in a hazardous environment and there presently exists no known automated robot mining apparatus that can follow a vein of mineralization without operator guidance and/or frequent manual testing of the mined ore to determine whether the desired vein of minerals is present at the mining face in front of the mining apparatus. Where the cross section of the vein of mineralization is of small dimensions, present operator guided machinery must remove a significant amount of ore, inclusive of the narrow vein, in order to mine the desired minerals. Where the materials are of a nature that sampling of the mined ore is required to determine the percent of mineralization of the material being mined, operators must frequently interrupt the mining process in order to identify the location of this narrow cross section vein if it meanders through the strata which is being mined. The degree of irregularity of the vein determines the frequency of sampling necessary to guarantee that the vein is followed by the mining apparatus. All of these operations are so inefficient and costly that it is the exception rather than the rule that a narrow vein of mineralization is commercially mined since the return in volume of useable mineral for the amount of ore removed and the amount of labor required to remove the ore render it uneconomical to retrieve the minerals in a narrow vein application. In the hazardous environment condition, it is also uneconomical to mine the ore even though the vein of mineralization may be significantly larger and susceptible to mining by operator guided machinery. The hazardous environment precludes the use of the operator and therefore obviates the possibility of retrieving the desired ore.

SOLUTION

The above described problems are solved and a technical advance achieved in the field by the automatic vein follower for robot mining apparatus of the present invention. This apparatus dynamically identifies the presence of the desired minerals, the percent of mineralization of the vein being followed and guides the operation of a robot mining apparatus to follow the vein of mineralization independent of operator intervention. The presence of the desired mineral is determined by the use of a screening method which relies on the spectral signature created by the reflected, and/or refracted and/or luminous light transmitted from the mining face. The mining face is illuminated using a broad spectrum light source and the returned illumination is filtered through a plurality of narrow band light filters to provide an indication of the light intensity of the reflected light at various frequencies, which frequencies are selected to be uniquely indicative of the desired mineral or minerals. The relative light intensity received from each of the filters is compared with known mineral signatures by a processor in order to identify the presence of the desired mineral as well as the percent of mineralization of the vein at the mining face. A video camera system is used to provide an image representative of the entire mining face, which image is used to identify not only the presence and quantity of the desired mineral but also its location on the face being mined by the robot mining apparatus. Various mathematical techniques are used, such as center of mass and end point bounding, to orient the center of the mining operation in an area that corresponds to the center of the vein of mineralization. These determinations are performed on a dynamic basis so the robot mining apparatus continually follows the vein of mineralization even though it may follow a tortuous path through the surrounding strata. In this manner, an operator is not required to guide the robot mining apparatus and veins of fairly small dimensions, too small to enable the presence of an operator, can be mined without requiring the removal of a large amount of ore in order to accommodate the present operator guided mining equipment. Therefore, the ore extracted from the mine by the robot mining apparatus provides the highest percentage of mineral to host rock since the extraneous surrounding host rock is not removed to merely accommodate the dimensions of the operator guided mining apparatus that is presently in use. The robot mining apparatus can be sized to accommodate the dimensions of the vein of mineralization and is independent of the needs of an operator since the present apparatus controls the operation of the robot mining apparatus and does not necessitate the presence of an operator nor the need to periodically sample the ore being mined in order to identify the presence of the desired mineral. It is obvious that this apparatus can also be used in a hazardous environment since it typically would not be sensitive to ambient conditions that are hazardous to a human operator.

DETAILED DESCRIPTION

In mining operations, it is economical to retrieve minerals from subsurface mines only when the size and purity of the vein of minerals is of sufficient magnitude to justify the cost of the quantity of ore necessitated by the present mining machinery and the processing of this quantity of ore to retrieve the desired minerals. The size of the present day mining machinery is dictated to a large extent by the need to have a human operator guide and operate the mining machinery. Therefore, veins of small cross section and veins which follow a tortuous path through the strata are uneconomical to mine since a small vein necessitates the removal of a large quantity of ore due to the need to have a human operator guide the mining machine. A large quantity of ore must then be processed with the ensuing large quantity of tailings in order to retrieve the small quantity of desired minerals. Furthermore, if the vein follows a tortuous path through the strata, mining must be halted on a frequent basis to enable manual testing to be performed on the mining face to ensure that the mining machine is indeed following the course of the vein through the strata. These tests presently performed are time consuming and inefficient due the need to cease mining operations in order to perform the test and await the test results before mining is again undertaken. Therefore, narrow veins of mineralization, especially those that follow a tortuous path through the strata, are not presently mined since the mining of such minerals is horribly expensive due to the inefficiencies and limitations of present day mining techniques.

Automated Vein Follower Concept

Figure 1:
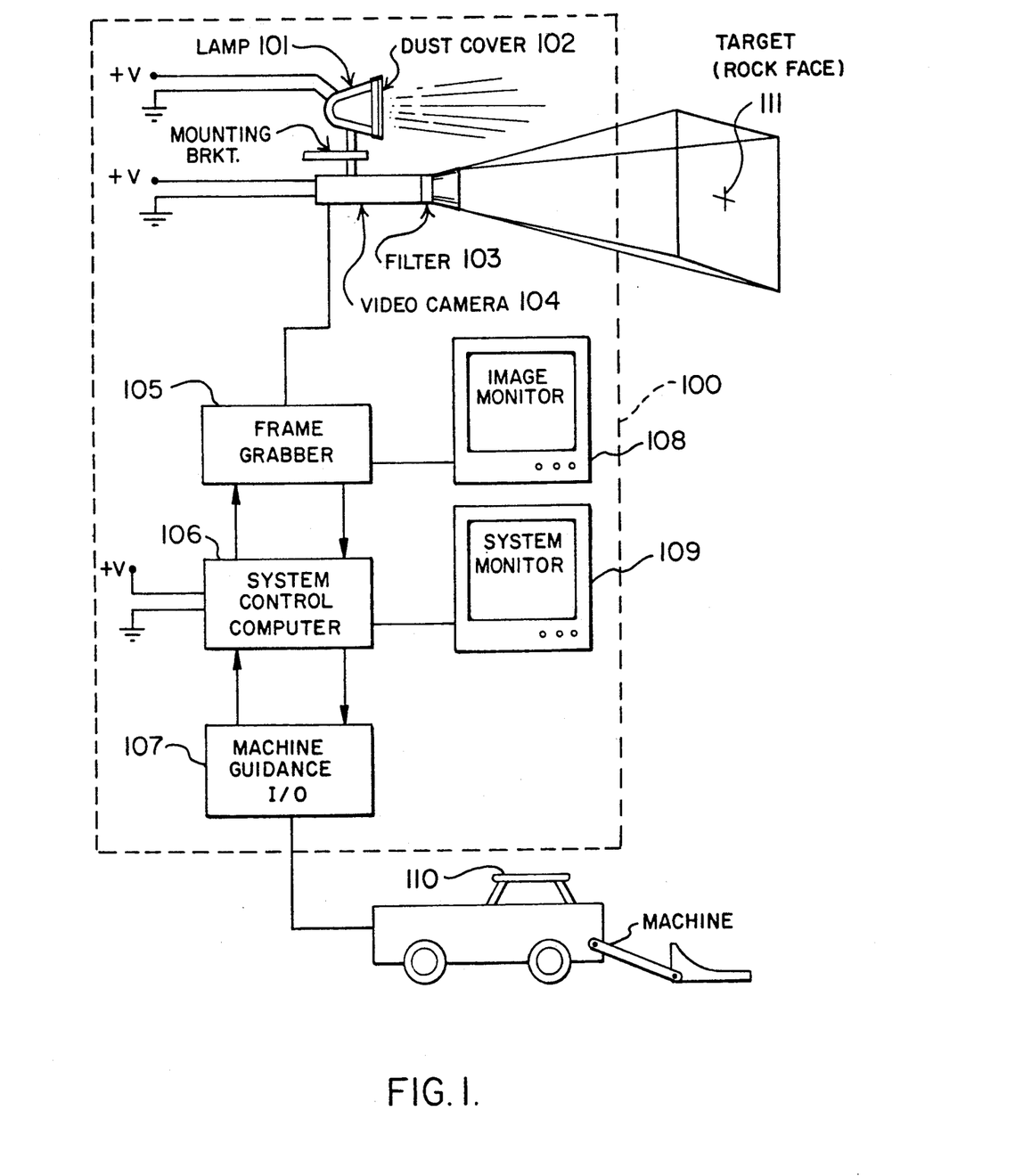
FIG. 1 illustrates in block diagram form the structure of the present automatic vein follower and its operational environment.
Figure 2:
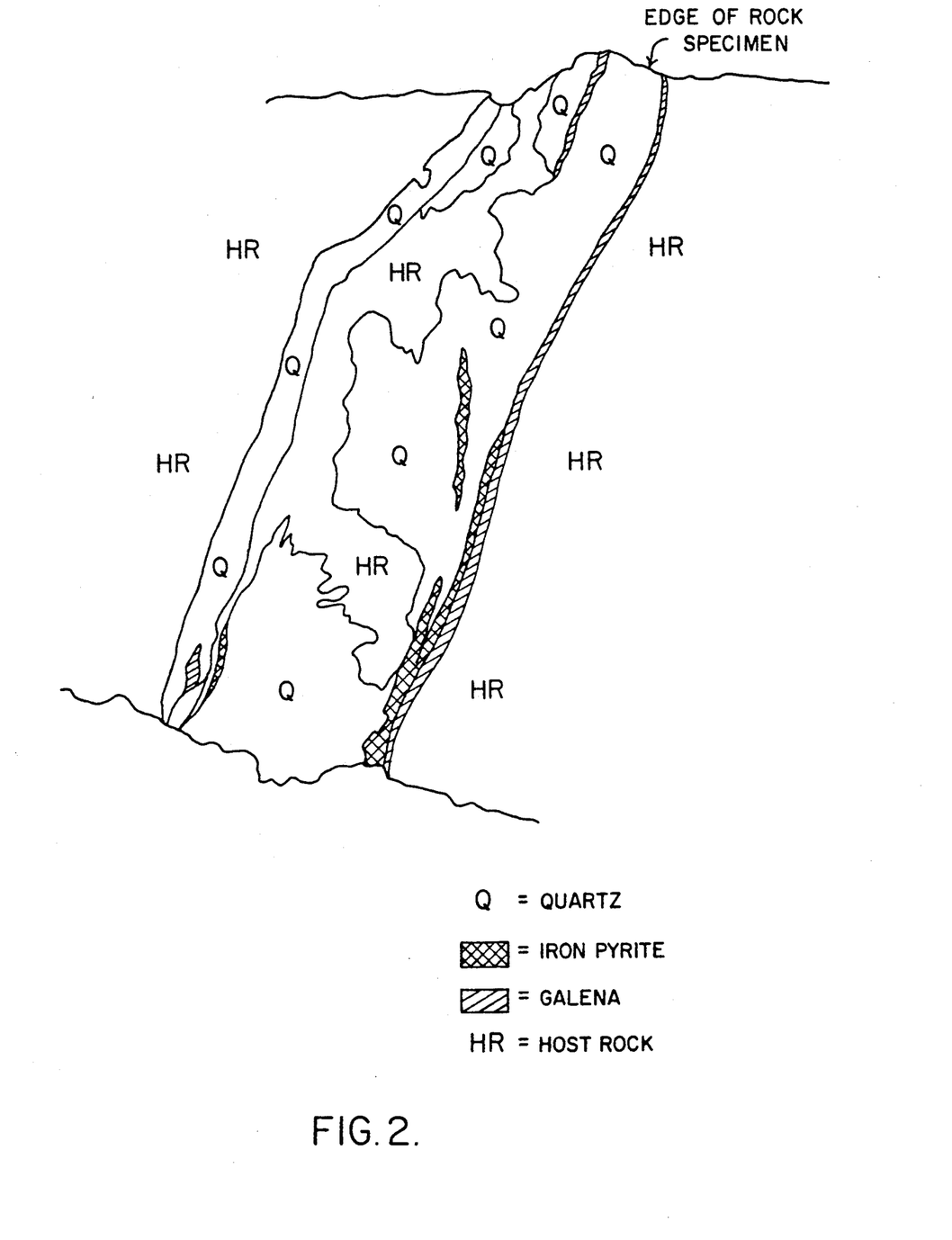
FIG. 2 illustrates a diagram of a typical vein cross section.

The automatic vein follower of the present invention is illustrated in block diagram form in FIG. 1 in its typical application of guiding a robot mining apparatus to follow a narrow vein of mineralization as illustrated in FIG. 2 and mine this vein using the robot mining apparatus. A light source is used to illuminate the mining face, where the term mining face identifies the wall of material on which the robot mining apparatus operates to retrieve the ore from the surrounding strata. It is well known that minerals have unique electronic, acoustic, and light reflective properties by which the minerals can be uniquely identified. A significant amount of research has been done in this area in order to provide methodologies to uniquely identify component minerals in a mixture. However, all presently known systems operate in a laboratory environment or simply provide gross characterizations of classes of materials present on a geologic scale. There is no known practical mining equipment that can dynamically identify minerals in an operational mine environment.

The present apparatus makes use of a novel mineral identification system to not only identify the desired minerals and estimate the percent of mineralization of the vein, but also locate their presence on the mining face in an x, y coordinate manner in order to guide the mining operation of the associated robot mining apparatus. This is accomplished through the use of a camera and video monitor system which picks up the light reflected, refracted or luminesced off the mining face as illuminated by the light source. Therefore, on a pixel by pixel basis the camera identifies the light intensity transmitted from the mining face. In order to obtain the unique light signature of the desired minerals, a plurality of narrow band light filters is used to screen the light transmitted from the mining face prior to its being focussed on the video camera. Thus, a three dimensional matrix is formed, consisting of data entries for each pixel of the video image for each frequency of interest as determined by the filter used to filter the transmitted light prior to its focussing onto the video camera. By comparing the light intensities at the various frequencies selected by the system with previously stored unique mineral signature data stored in the processor memory, the processor can identify the presence and location of the desired minerals on the mining face. For each pixel position in the x, y direction, the processor creates a series of z direction data points each of which corresponds to a particular light frequency. For each pixel, a collection of z direction data points that match the unique signature associated with the desired mineral is indicative of the presence of the desired mineral and is included in the vein of mineralization on the mining face. Additionally, the percentage of mineralization can be determined by calculating the percentage of total pixels in the vein within the field of view of the camera that match the unique signature of the desired mineral.

System Architecture

FIG. 1 illustrates in schematic diagram form the architecture of the automatic vein follower of the present invention. The automatic vein follower 100 consists of a plurality of elements that are used to identify the presence and location of the vein of mineralization on a target rock face 111 which is being mined by an automated machine 110. The automatic vein follower 100 consists of a video camera 104 which is equipped with a plurality of filters 103 and a lamp 101 with an associated dust cover 102. Video camera 104 is focused on the target rock face 111 which is illuminated by lamp 101. The output of the video camera 104 is a video image of the illuminated rock face 111 which is captured by frame grabber 105 and input to system control computer 106 where it is stored for data processing. An image monitor 108 provides a display representative of the output of video camera 104. System monitor 109 provides a user interface to control the operation of the automatic vein follower 100 or to reprogram same. Machine guidance input/output system 107 receives control signals from system control computer 106 and converts these into guidance signals to control the operation of automated mining machine 110. It is obvious that a number of these elements must be co-located or mounted on the automated mining machine 110. In particular, video camera 104 with its associated filters 103, lamp 101 and dust cover 102 must be present at the target rock face 111 which is being mined by automated mining machine 110. The output signals from video camera 104 can be directly transmitted to frame grabber 105 via direct cable link as is illustrated in FIG. 1 or can be transmitted via wireless connection (not shown) to a site where the control electronics (105, 106, 108, 109) are located. In this situation, machine guidance system would similarly be connected to the automated mining machine control electronics (105, 106, 108, 109) via a wireless link to transmit signals therebetween. These specific interconnects are simply implementation details and are not discussed at length herein.

Lamp 101 is a high power broad spectrum light source that is used to illuminate the target rock face 111. The light reflected, refracted or luminesced from target rock face 111 is received by video camera 104 through one of a plurality of filters 103. Filters 103 consist of a plurality of narrow band filters which are switchably interposed between the light received from target rock face 111 and video camera 104. The use of the plurality of filters 103 enables the automatic vein follower system 100 to take a plurality of images of a target rock face 111 with each of these plurality of images representing a narrow band view of the light received from target rock face 111. This plurality of images received through the use of the plurality of filters 103 are then used to produce a signature for the various segments of the target rock face 111 to be compared with signatures stored in system control computer 106, each of which is indicative of a standard mineral. When the received images match a stored signature, system control computer 106 determines the presence of that mineral at the particular location on target rock face 111. The presence of a plurality of these locations indicate a vein of mineral and it is this vein that automated mining machine 110 must follow in the mining process.

Figure 3:
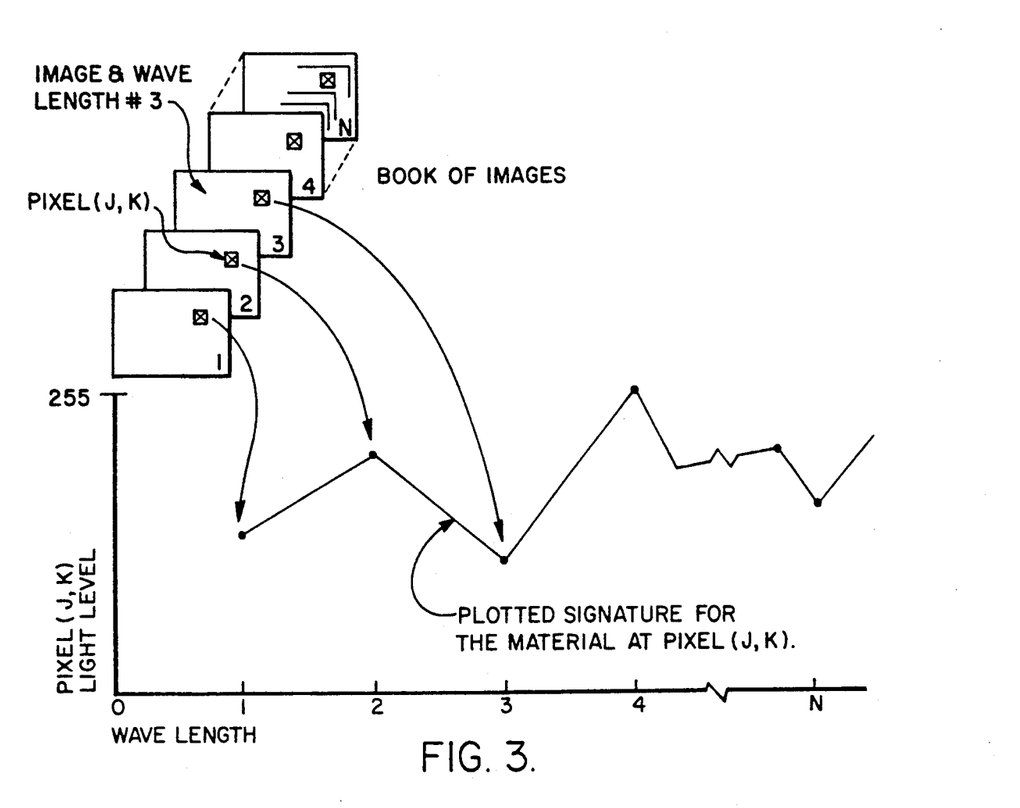
FIG. 3 illustrates in block diagram form the signature mapping process.
Figure 4:
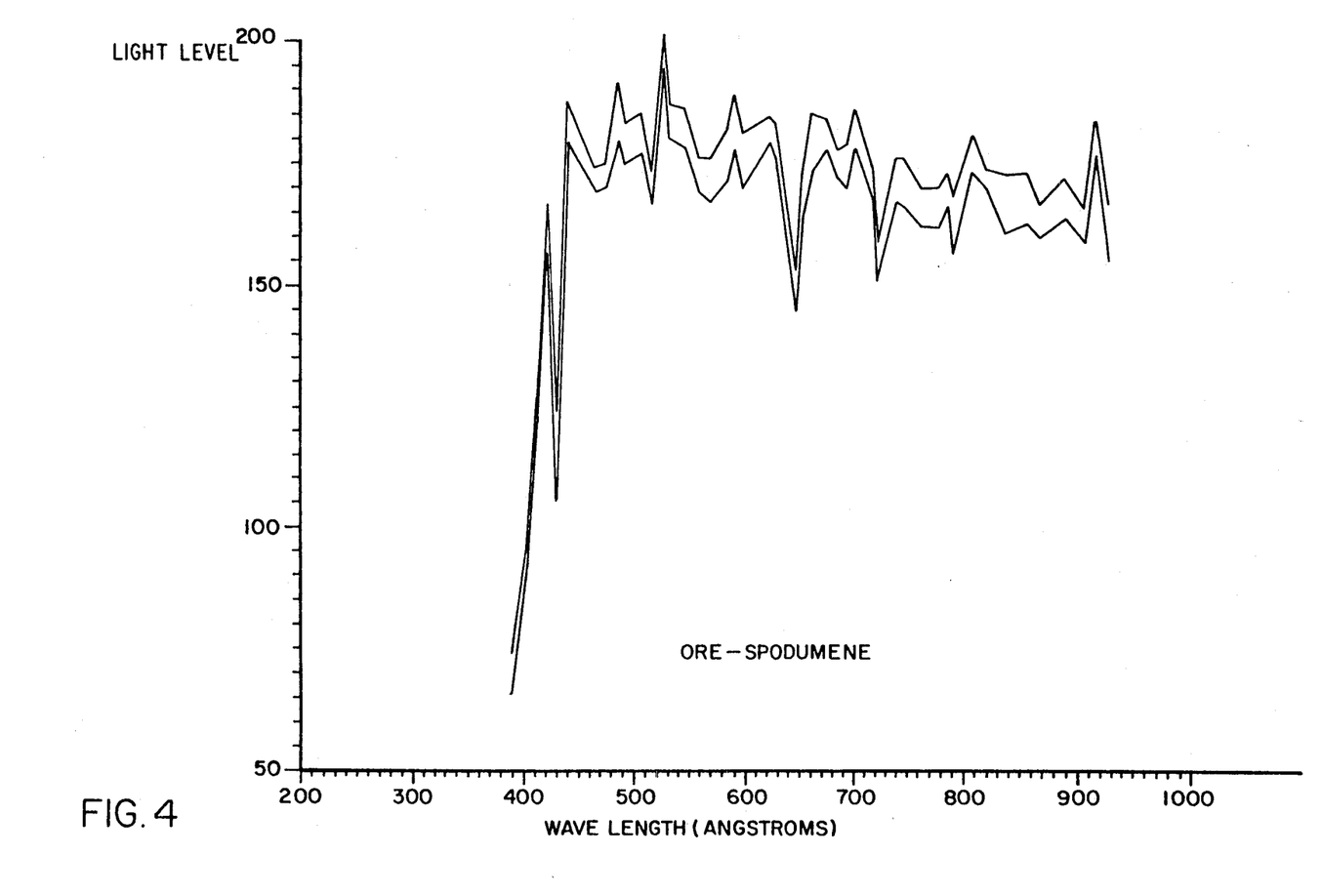
FIG. 4 illustrates typical mineral signature data in graphical form.
Figure 5:
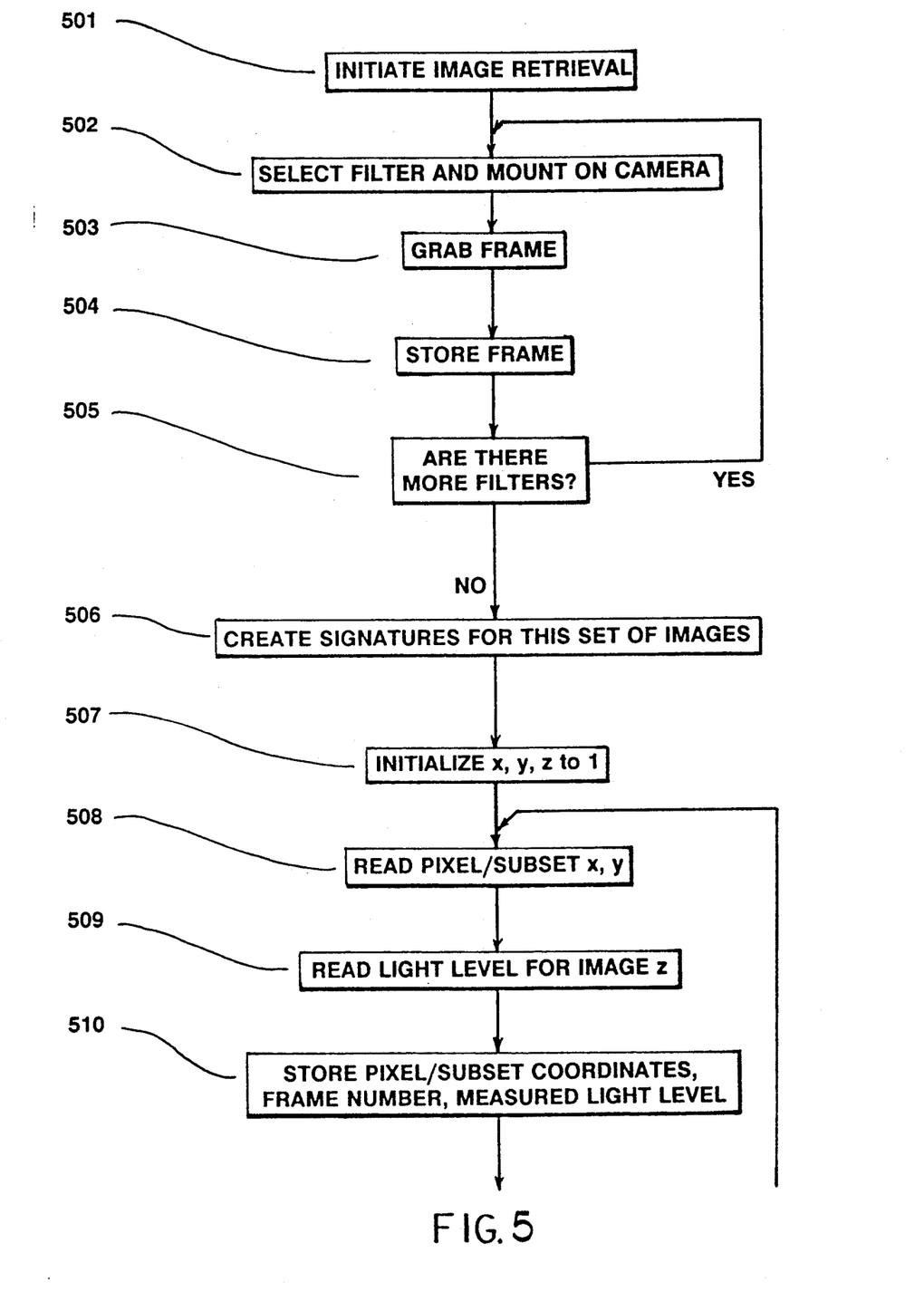
FIGS. 5-8 illustrate in flow diagram form the operational steps taken by the control apparatus within the automatic vein follower to guide the operation of the associated robot mining apparatus.
Figure 6:
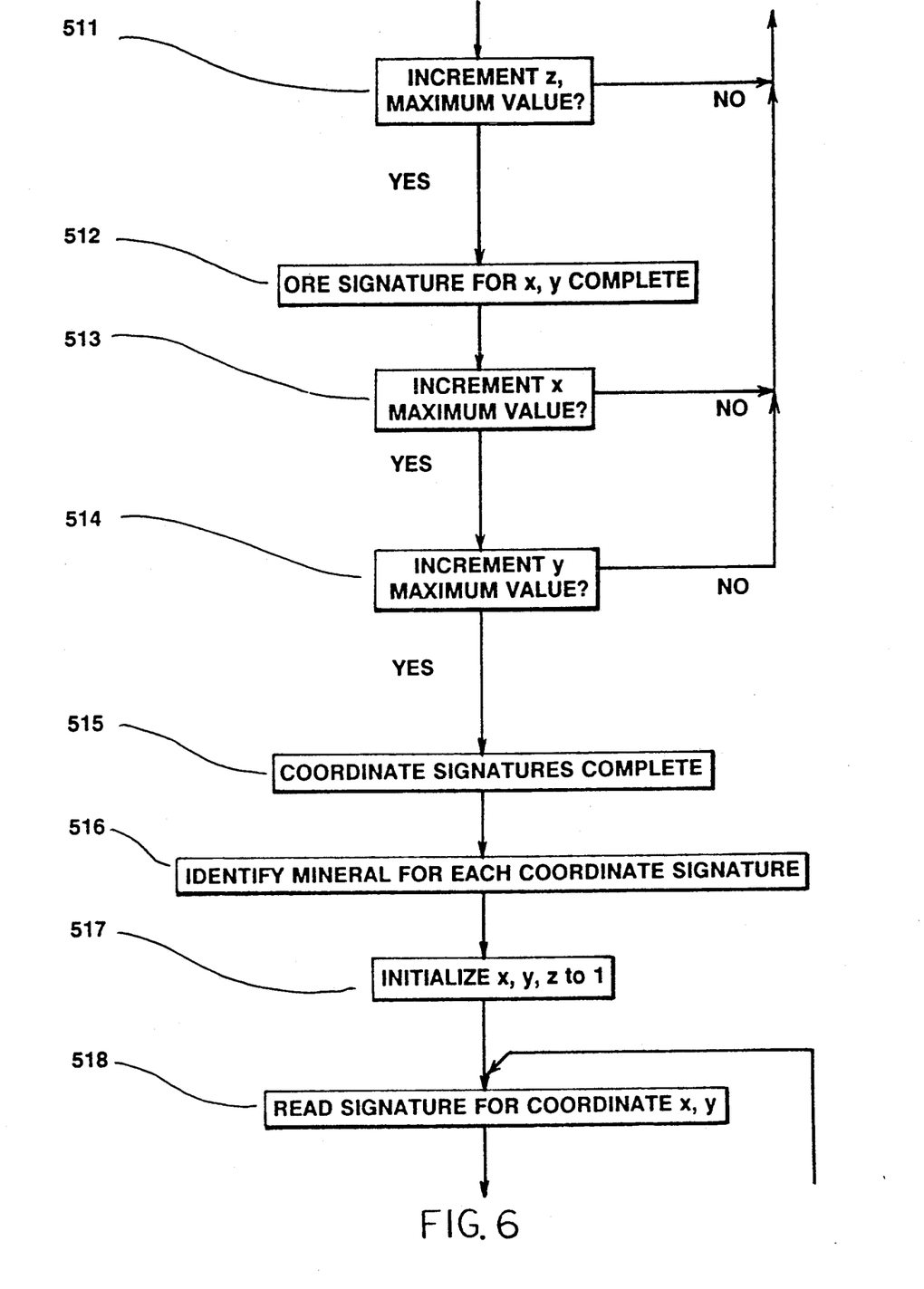
Figure 7:
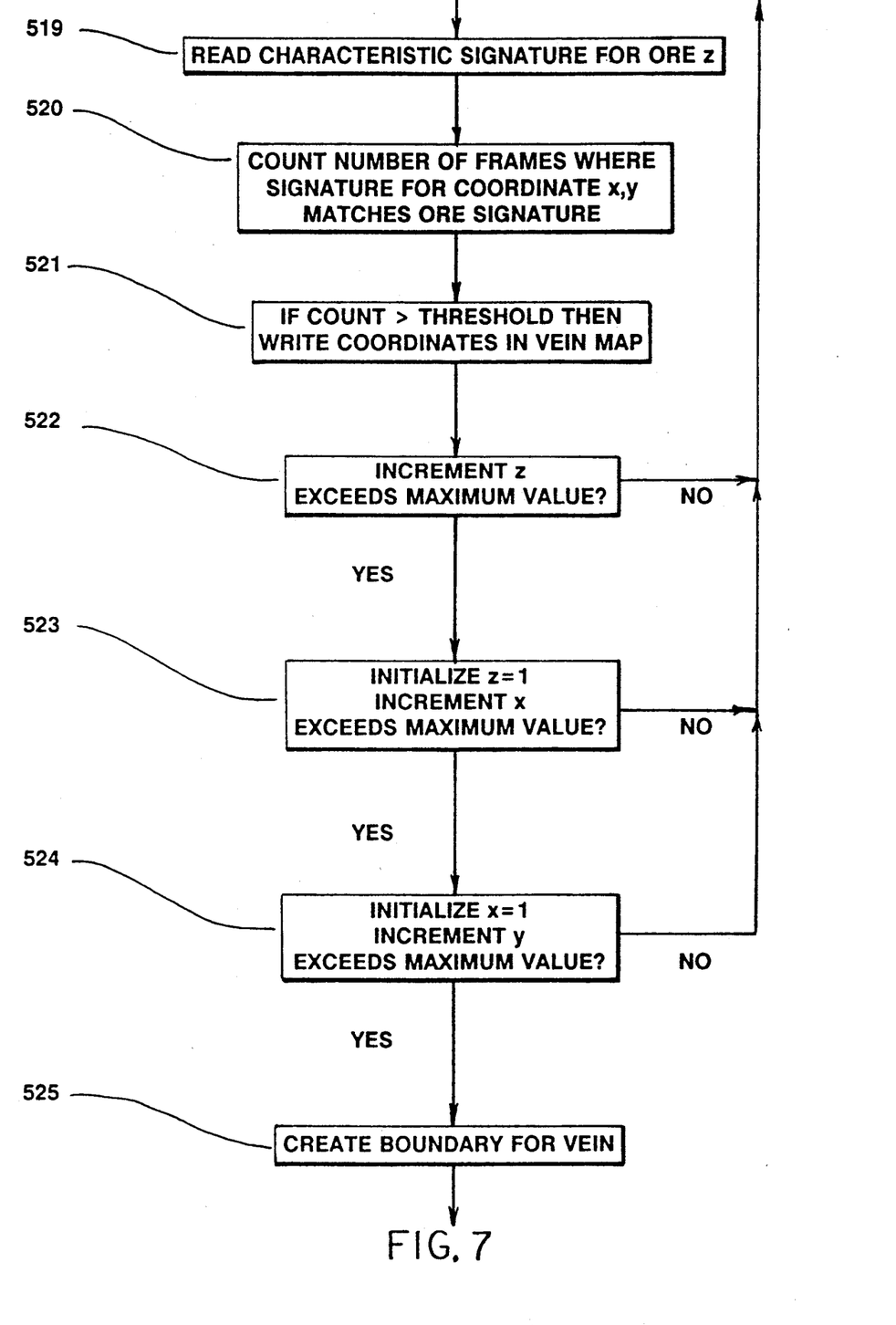
Figure 8:
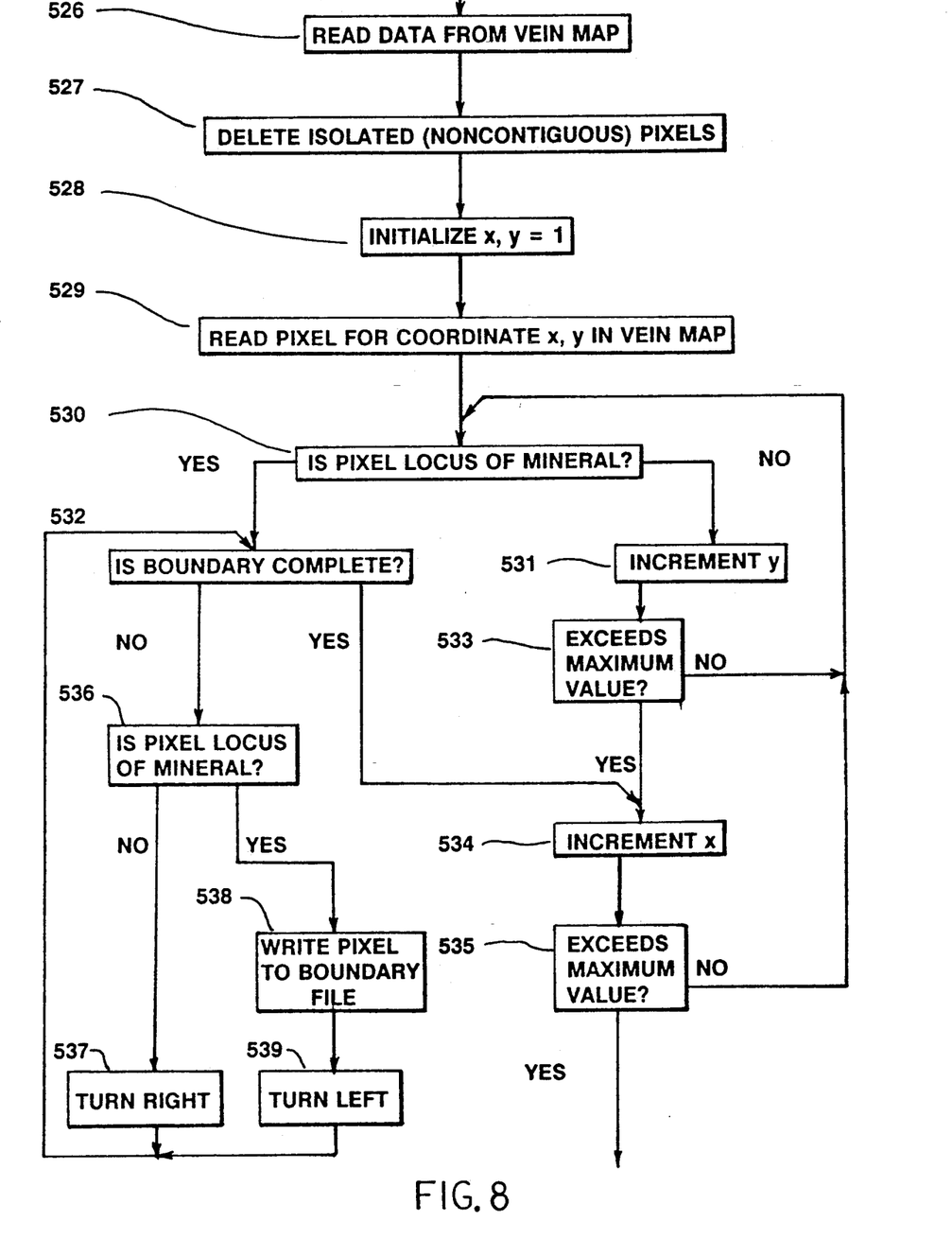

FIG. 3 illustrates a conceptual view of this process. Frame grabber 105 stores the video image frame produced by video camera 104 for each of the filters 103 that is interposed between video camera 104 and the light transmitted from target rock face 111. Each of the stored images or frames 200-1 to 200-n as illustrated in FIG. 3 consists of a plurality of pixels, with each pixel representing a particular location on the target rock face 111. By plotting the same pixel coordinate location from each of the plurality of stored images onto a chart as is illustrated in FIG. 4, a characteristic signature for the material at pixel j, k is produced. This characteristic signature consists of a transmitted light level at various wave lengths, with each of the wave lengths representing one of the plurality of filters 103. This plotted signature can then be compared with a characteristic signature for various minerals. In operation, a plurality of pixels at a particular location can be used to obtain a composite signature for a segment of the target rock face 111. For example, nine signatures consisting of a 3×3 mask centered around a particular pixel can be averaged or used to produce an envelope signature representative of the high and low values of the nine pixels that represent the subset or locus on the target rock face 111. Table 1 illustrates typical set of data collected for the nine pixels around a particular location for the ore spodumene. Table 1 also illustrates the wave length of the transmitted light that is passed through the associated filter 103 as well as the envelope values consisting of the high and low values of the nine signature values obtained from the nine pixels. The envelope obtained from this calculation is then plotted in FIG. 4 to illustrate the raw data indicative of the nine pixels analyzed at this particular target rock face 111.

Operational Steps - Mineral Identification Data Collection

FIGS. 5-8 illustrate in flow diagram form the operational steps taken by the control apparatus within the automatic vein follower to guide the operation of an associated robot mining apparatus. At step 501, system control computer 106 initiates the image retrieval process. This consists of system control computer 106 at step 502 transmitting control signals to the image input device 120 which consists of the video camera 104, filters 103, lamp 101 and dust cover 102. These control signals from system control computer 106 activate the filter selection apparatus to insert a selected filter 103 on video camera 104 to thereby interpose filter 103 between video camera 104 and target rock face 111 to thereby selectively pass only the narrow band of frequencies associated with this filter to video camera 104. At step 503, system control computer 106 activates frame grabber 105 to record the image produced by video camera 104. This image consists of a picture of the target rock face 111 as seen at the particular narrow band of frequencies passed by filter 103. This selective illumination of target rock face 111 presents one element of the characteristic signature of target rock face 111. Frame grabber 105 at step 504 stores this image in memory for later retrieval and processing. At step 505, system control computer 106 determines whether there are more filters to be used to generate the book of images required to determine characteristic signature of the minerals in target rock face 111. If more filters are required, system control computer 106 returns to step 502 and repeats steps 502-505 in order to produce a plurality of images which are stored in frame grabber memory 105 to produce a book of images each which represents the characteristic image of target rock face 111 at a selected narrow band of frequencies. This book of images thereby represents the characteristic signature of target rock face 111 as seen in n*m pixels of data per frame.

Once all the filters of interest have been used by system control computer 106 to obtain the necessary book of images, system control computer 106 proceeds to step 506 and activates the create signatures subroutine for this set of images that are stored in frame grabber 105. At step 507, system control computer 106 initializes the variables x, y and z to a value of one. At step 508, system control computer 106 reads the pixel or subset of pixels designated by the coordinates x, y which in this case would be 1, 1. At step 509, system control computer 106 retrieves the light level data stored for this set of coordinates for image z which in this case is 1. At step 510, system control computer 106 stores the pixel/subset coordinates, frame number and measured light level in memory. At step 511, system control computer 106 increments the variable z to thereby retrieve the light level at this particular set of coordinates for the next image stored in the memory of frame grabber 105. When z is incremented, system control computer 106 returns to step 509 and retrieves the light level data stored in the memory of frame grabber 105 for the subsequent image. Steps 509-511 are repeated in order to produce the characteristic signature of target rock face 111 at the particular set of coordinates x, y. In this manner, the location on target rock face 111 corresponding to the coordinates x, y associated with pixel or subset x, y can be analyzed using the signature produced by this process.

At step 512 the ore signature for coordinates x, y is complete and this signature consists of a plurality of data points, each of which represents the level of reflected, refracted, luminesced light at the particular defined frequency. In order to analyze the entirety of the illuminated area on target rock face 111 at steps 513 and 514, system control computer 106 proceeds to increment x from the value of one through its maximum value followed by the variable y which is also incremented from one to its maximum value. In this manner, system control computer 106 creates a characteristic signature for every location on target rock face 111 that corresponds to the pixels or subsets x, y that are stored in the memory of frame grabber 105.

These signatures can be for every pixel in the image produced by the video camera 104 or can represent subsets of the entirety of the pixels where the pixels are grouped into contiguous or even noncontiguous groupings in order to reduce the processing time required to determine the presence and location of minerals on the illuminated target rock face 111. For example, as noted above and as shown in Table 1, a block of nine pixels can be processed in order to produce an envelope signature consisting of the maximum and minimum values of the measured light levels at the selected frequencies to obtain a envelope type of signature as illustrated in FIG. 4. Therefore, the incrementing of the variables x and y are such that blocks of nine pixels at a time are processed and instead of a single pixel signature, an envelope signature is produced. At step 515 the generation of the characteristic signatures for each of the coordinates in the image is complete.

Operational Steps - Mineral Identification

At step 516, system control computer 106 begins the identification of minerals for each of the coordinate signatures stored in memory. This is accomplished by initializing variables x, y and z to a value of one at step 517. At step 518, the characteristic signature stored in the memory of system control computer 106 for the coordinates x and y is read from memory. At step 519, system control computer 106 reads the characteristic signature for one of the minerals or ores of interest. At step 520, system control computer compares the two characteristic signatures by comparing the number of frames where the signature for the coordinate x, y matches the corresponding ore signature. This process consists of a frequency by frequency comparison of the current pixels with the values stored in memory for a known ore at corresponding frequency. This comparison at coordinates x, y matches the reflected, refracted, luminesced light level at each frequency with the corresponding envelope for each ore being analyzed. The number of frames or frequencies where the two signatures correspond represents an indication of how closely the mineral on the target rock face 111 corresponding to coordinates x and y match the ore of interest. The correspondence can be determined in any of a number of ways. For example, if the envelope produced in the envelope process noted above is such that the characteristic signature for the ore presently being analyzed falls within the envelope generated for this subset of coordinates, then a match can be said to occur. Where a single pixel is being compared to the characteristic ore signature, the two light levels differ by less than a predetermined amount, a correspondence can be said to occur. At step 521, system control computer 106 sums the total number of frames where the two signatures correspond and, if this count exceeds a predetermined matching threshold, then the coordinates x and y are noted as having the mineral of interest present. This is accomplished by writing a data point on a vein map at the location corresponding to the coordinates x, y. By producing this set of data points in the form of a vein map, a picture is painted by the vein follower indicative of locations where the mineral of interest is present. In the case of a plurality of ores being co-located in the target rock face 111, system control computer 106 proceeds to step 522 and increments the variable z to repeat the characteristic signature comparison process for the next mineral of interest. Once all of the minerals of interest or ores stored in memory are compared to characteristic signature for the coordinates x, y, processing proceeds to step 523 where system control computer 106 re-initializes the variable z to be equal to one and increments the variable x. This causes the processing to retrieve the signature for the next coordinate in the set of coordinates stored in the memory of frame grabber 105. The resetting of the variable z causes the first mineral of interest to be again compared to the signature for the coordinates now being analyzed by system control computer 106. Similarly, at step 524, system control computer 106 initializes x to be equal to one and increments y to thereby proceed through the next row of coordinates in the images stored in frame grabber 105. By proceeding through steps 518-524, all of the coordinates determined to have the mineral or minerals of interest present are written into the vein map which thereby illustrates both the presence and location of the minerals on the target rock face 111.

Operational Steps - Vein Definition

In order to use this information in a dynamic fashion to control automated mining equipment, at step 525 system control computer 106 initializes the boundary creation process to thereby define the meets and bounds of the vein of mineralization. At step 526, system control computer 106 reads the data from the vein map and deletes in step 527 isolated pixels which represent pixels indicative of the presence of the mineral which pixels are not adjacent to another pixel indicating the presence of a mineral. Once the isolated or noncontiguous pixels have been eliminated from the vein map, system control computer 106 at step 528 initializes the variables x, y to equal one. At step 529, system control computer 106 reads the pixel for the coordinates x and y in the vein map. If this pixel contains data indicative of the locus of the mineral of interest, at step 530 processing proceeds to determine at step 532 whether the boundary of the vein has been completed in that the boundary line that is being drawn has reached the starting point. If the boundary is not complete, processing proceeds to step 536 where system control computer 106 determines whether this particular pixel is the locus for minerals of interest. If it is, at step 538 system control computer 106 writes this pixel into a boundary file and step 539 turns left by reading the data point for the pixel adjacent to the present pixel but on the left hand side of the line of pixels presently being followed. Processing then returns step 536 to determine whether this new pixel also contains a mineral. If it does processing continues through 538, 539 and back to 536 to attempt to create an envelope around the area of mineralization. Once a pixel that does not contain a mineral is located, the direction of movement of the boundary is changed at step 537 to turn right, or a 90° direction change from the present line of movement. Processing then returns to step 532 to determine whether the boundary is complete. This process of steps 532, 536-539 is repeated until the boundary of this set of pixels containing minerals is completed.

Once the boundary is complete, processing proceeds to step 534 where the variable x is incremented and if this does not exceed the maximum value for x, processing returns from step 535 to step 529 where again data for this particular coordinate x, y is read from the vein map to determine whether minerals are present at this location. When no data is present in the vein map at this location indicative of the presence of minerals, the variable y is incremented by system control computer 106 at 531 and if this does not exceed the maximum value at step 533, processing returns to step 530 in order to cycle through all of the pixels in this particular row. If no minerals are located in analyzing this row, the variable x is incremented at step 534 and, if this is not the last row as determined at step 535, processing returns to step 529 to repeat the process for the entirety of the vein map.

An alternative method of defining the boundary of the vein of mineralization is to read, on a row-by-row basis, each pixel on the image. The data value assigned to each pixel is indicative of the presence or absence of the desired mineralization. If the data value for a read pixel matches the desired mineralization, it is retained, otherwise the data value is set to zero. Thus, this process eliminates all data points that do not match the desired mineralization, leaving only an image of the vein of interest.

Vein Map

Figure 9:
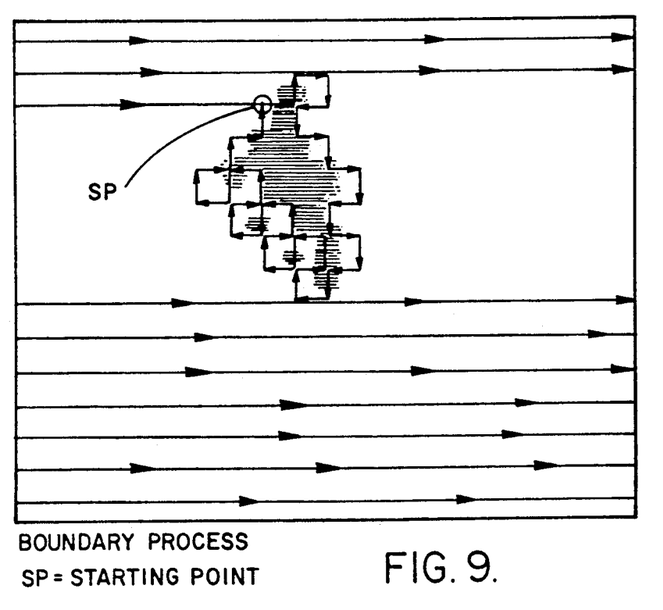
FIG. 9 illustrates in graphical form the operation of the boundary process.
Figure 10:
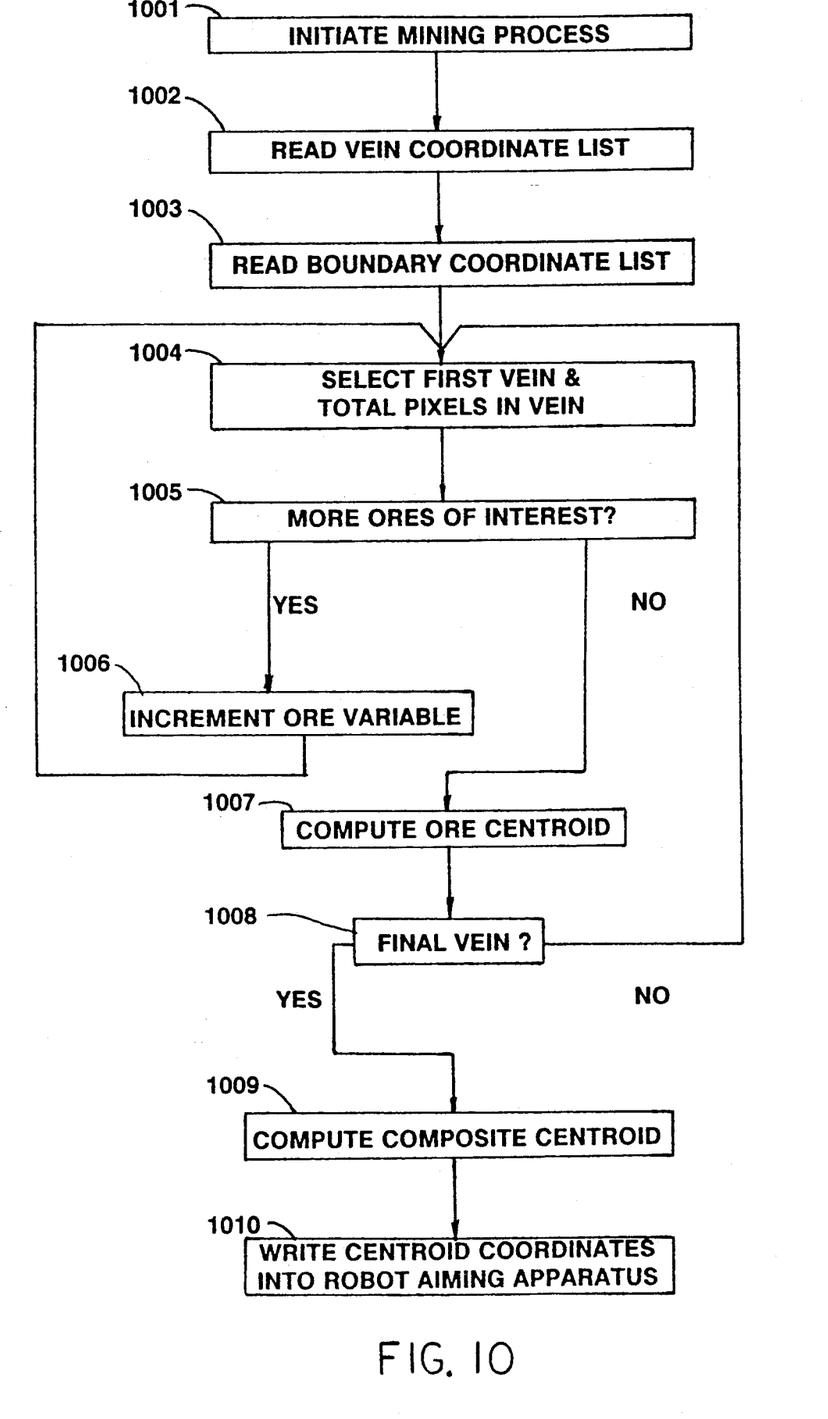
FIG. 10 illustrates in flow diagram form the operation of the robot mining apparatus guidance process.

The results of this bounding process is illustrated in FIG. 9 wherein each vein or region containing minerals of interest are defined by boundary lines created by the automated vein follower apparatus using the process described above. Once all of the boundaries have been mapped using this procedure, this data can be used to guide the operation of a robot mining apparatus. This guidance procedure is illustrated in flow diagram form in FIG. 10. At step 1001, the process is initiated by system control computer 106 which functions to control the operation of a robot mining apparatus 110 through interface or machine guidance input/output device 107. At step 1002, system control computer 106 reads the coordinate list which identifies all the vein areas determined at described above. In addition, at step 1003 system control computer 106 reads the coordinate list which define the boundaries as calculated using the boundary definition process described above. At step 1004, system control computer 106 selects the first vein area that has been read from memory and totals the number of pixels bounded by the defined boundary. At step 1005, system control computer 106 determines whether there are more ores of interest than the particular one whose total was calculated. If there are a plurality of ores of interest, at step 1006, the ore variable is incremented and the totaling process is repeated until a total is calculated for each of the ores of interest in this particular bounded vein area. Once this totaling process is complete, at step 1007, the area centroid is computed using well known mathematical techniques. At step 1008, system control computer determines whether this is the final vein that was bounded by the above noted process. If not, steps 1004–1008 are repeated to compute the area centroid for each of the vein areas in the image or vein map created. Once the vein areas have been analyzed in this manner, at step 1010, system control computer 106 computes the composite centroid for all areas in the vein map. This centroid identifies the center of mass or most densely mineralized area of the vein. At step 1011, the centroid coordinates are written into an aim process in order to control the guidance of the associated robot mining apparatus 110.

Percent of Mineralization

In addition to this guidance function, the percent of mineralization can be determined by simply computing the relative numbers of pixels representative of the presence of a particular mineral as compared to the total number of pixels in the vein. This can be done for each of the ores or minerals of interest in order to identify the percent of mineralization of vein on the illuminated rock face 111. In this manner, not only is the presence of various minerals dynamically determined by this apparatus, but the percent of mineralization on the particular illuminated mining face is determined and this information is used to guide the operation of an associated robot mining apparatus independent of operator intervention.

While a specific embodiment of this invention has been disclosed, it is expected that those skilled in the art can and will design alternate embodiments of this invention that fall within the scope of the appended claims.

TABLE 1

CAMERA JAVELIN 2362
LIGHTING SP + IL
ORE SPODUMENE
DATE 12-29-89
PIXELS 9 @ (424,128)

| A | ************LIGHT LEVEL******** | | | | | | | | LOW | HI |
|---|---|---|---|---|---|---|---|---|---|---|
| 930 | 161 | 158 | 162 | 158 | 159 | 156 | 167 | 165 | 160 | 156 | 167 |
| 920 | 181 | 182 | 179 | 180 | 184 | 182 | 180 | 177 | 177 | 177 | 184 |
| 909 | 164 | 165 | 159 | 163 | 160 | 160 | 166 | 166 | 160 | 159 | 166 |
| 892 | 171 | 167 | 164 | 169 | 172 | 169 | 165 | 169 | 166 | 164 | 172 |
| 870 | 164 | 163 | 166 | 166 | 161 | 163 | 167 | 162 | 160 | 160 | 167 |
| 858 | 169 | 167 | 163 | 165 | 169 | 169 | 168 | 173 | 170 | 163 | 173 |
| 840 | 164 | 168 | 161 | 168 | 173 | 169 | 169 | 170 | 170 | 161 | 173 |
| 821 | 170 | 173 | 171 | 173 | 172 | 170 | 171 | 174 | 174 | 170 | 174 |
| 809 | 177 | 173 | 178 | 181 | 181 | 178 | 174 | 175 | 173 | 173 | 181 |
| 792 | 164 | 168 | 163 | 167 | 164 | 163 | 157 | 162 | 165 | 157 | 168 |
| 788 | 168 | 166 | 169 | 172 | 173 | 170 | 167 | 167 | 167 | 166 | 173 |
| 780 | 167 | 162 | 170 | 165 | 162 | 170 | 165 | 162 | 163 | 162 | 170 |
| 766 | 162 | 164 | 164 | 170 | 169 | 164 | 165 | 165 | 164 | 162 | 170 |
| 748 | 173 | 173 | 170 | 174 | 176 | 171 | 172 | 173 | 166 | 166 | 176 |
| 741 | 173 | 176 | 167 | 172 | 173 | 174 | 168 | 170 | 171 | 167 | 176 |
| 724 | 159 | 158 | 155 | 158 | 155 | 151 | 152 | 152 | 155 | 151 | 159 |
| 719 | 172 | 173 | 174 | 172 | 172 | 168 | 170 | 171 | 169 | 168 | 174 |
| 703 | 186 | 182 | 179 | 178 | 179 | 185 | 179 | 178 | 180 | 178 | 186 |
| 696 | 171 | 171 | 178 | 178 | 179 | 172 | 170 | 170 | 170 | 170 | 179 |
| 688 | 178 | 172 | 176 | 177 | 178 | 177 | 172 | 177 | 172 | 172 | 178 |
| 678 | 182 | 180 | 179 | 182 | 184 | 183 | 183 | 182 | 178 | 178 | 184 |
| 665 | 184 | 182 | 178 | 182 | 185 | 178 | 173 | 176 | 178 | 173 | 185 |
| 656 | 166 | 164 | 169 | 171 | 167 | 167 | 169 | 172 | 164 | 164 | 172 |
| 649 | 146 | 146 | 151 | 153 | 148 | 147 | 145 | 145 | 150 | 145 | 153 |
| 630 | 181 | 180 | 182 | 183 | 183 | 181 | 176 | 179 | 181 | 176 | 183 |
| 625 | 184 | 180 | 180 | 181 | 183 | 184 | 181 | 182 | 179 | 179 | 184 |
| 599 | 181 | 177 | 170 | 170 | 174 | 177 | 173 | 180 | 181 | 170 | 181 |
| 592 | 183 | 179 | 183 | 188 | 185 | 189 | 181 | 177 | 180 | 177 | 189 |
| 586 | 173 | 171 | 173 | 181 | 182 | 173 | 173 | 178 | 177 | 171 | 182 |
| 572 | 176 | 167 | 174 | 174 | 176 | 173 | 171 | 172 | 170 | 167 | 176 |
| 562 | 176 | 169 | 173 | 173 | 171 | 176 | 173 | 172 | 170 | 169 | 176 |

TABLE 1-continued

CAMERA JAVELIN 2362
LIGHTING SP + IL
ORE SPODUMENE
DATE 12-29-89
PIXELS 9 @ (424,128)

| 549 | 183 | 178 | 182 | 186 | 183 | 185 | 181 | 183 | 185 | 178 | 186 |
|---|---|---|---|---|---|---|---|---|---|---|---|
| 535 | 187 | 180 | 187 | 183 | 181 | 186 | 186 | 183 | 180 | 180 | 187 |
| 530 | 199 | 201 | 198 | 200 | 199 | 197 | 197 | 198 | 194 | 194 | 201 |
| 518 | 171 | 168 | 173 | 170 | 167 | 173 | 171 | 170 | 168 | 167 | 173 |
| 509 | 177 | 178 | 185 | 183 | 181 | 180 | 179 | 181 | 181 | 177 | 185 |
| 494 | 183 | 175 | 181 | 181 | 176 | 179 | 178 | 176 | 180 | 175 | 183 |
| 488 | 183 | 180 | 182 | 191 | 189 | 184 | 182 | 186 | 186 | 180 | 191 |
| 477 | 175 | 174 | 174 | 174 | 170 | 173 | 172 | 174 | 174 | 170 | 175 |
| 467 | 171 | 174 | 170 | 172 | 171 | 172 | 169 | 173 | 172 | 169 | 174 |
| 442 | 183 | 183 | 187 | 187 | 185 | 180 | 179 | 182 | 183 | 179 | 187 |
| 431 | 121 | 115 | 114 | 119 | 124 | 116 | 111 | 109 | 106 | 106 | 124 |
| 423 | 166 | 162 | 160 | 163 | 162 | 166 | 163 | 159 | 156 | 156 | 166 |
| 415 | 122 | 125 | 124 | 126 | 123 | 121 | 125 | 126 | 124 | 121 | 126 |
| 403 | 96 | 92 | 95 | 94 | 91 | 95 | 94 | 93 | 92 | 91 | 96 |
| 390 | 67 | 72 | 66 | 72 | 73 | 71 | 74 | 73 | 66 | 66 | 74 |

We claim:

1. An automatic vein follower for dynamically identifying a vein of mineralization in a mine face comprising:
   means for generating a broad spectrum beam of light, which beam of light is aimed at said mining face to illuminate said mining face;
   means aimed at said illuminated mining face and responsive to said beam of light as returned from said illuminated mining face, for producing an n * m pixel image, with each pixel being representative of a returned light level from a corresponding location on said illuminated mining face, where n and m are positive integers greater than 1;
   a plurality of narrow bandwidth filter means, each transmissive of only a predefined range of frequencies of light;
   means for interposing a selected one of said narrow bandwidth filter means between said illuminated mining face and said producing means to block the transmission of all of said returned light beam, except said narrow band of frequencies passed by said selected narrow bandwidth filter means, from said illuminated mining face to said producing means;
   means for storing at least one mineral signature representative of the relative returned light level for a plurality of frequencies for a designated mineral;
   means for comparing said returned light level for at least one of said n * m pixels for a plurality of images, produced by sequentially interposing each of a plurality of said narrow bandwidth filter means between said illuminated mining face and said producing means, with at least one of said stored mineral signatures; and
   means responsive to said pixel for a predetermined number of said images being of illumination magnitude within a predetermined distance from said corresponding mineral signature value for identifying the presence of said mineral in said mineral face at a location thereon corresponding to said pixel.

2. The apparatus of claim 1 wherein each of said narrow bandwidth filter means is transmissive of only a predefined range of frequencies of light which range is centered about a center frequency corresponding to one of said plurality of mineral signature frequencies.

3. The apparatus of claim 1 further comprising:
   means for recording said plurality of images.

4. The apparatus of claim 3 wherein said comparing means sequentially compares all of said n * m pixels of all of said recorded images with said stored mineral signature to identify all the locations on said illuminated mining face containing said mineral.

5. The apparatus of claim 3 wherein said comparing means sequentially compares a predetermined subset of said n * m pixels of all of said recorded images with said stored mineral signature to identify all the locations on said illuminated mining face containing said mineral.

6. The apparatus of claim 3 wherein said comparing means includes:
   means for dividing said n * m pixels into a plurality of contiguous subsets, each of which contain j * k pixels, where j and k are positive integers greater than zero;
   means for generating an envelope representative of the maximum and minimum values of returned light for each subset for each image; and
   means for sequentially comparing all of said subset envelopes of all of said recorded images with said stored mineral signature to identify all the locations on said illuminated mining face containing said mineral.

7. The apparatus of claim 6 wherein said identifying means identifies the presence of said mineral in said mineral face at a location thereon corresponding to said pixel subset when said corresponding stored mineral signature value representative of the relative returned light level for the corresponding frequency falls within said envelope.

8. The apparatus of claim 1 further comprising:
   means for determining the centroid of said identified locations on said illuminated mining face containing said mineral.

9. The apparatus of claim 8 wherein said determining means includes:
   means for bounding all contiguous locations on said illuminated mining face identified as containing said mineral; and
   means for locating the centroid of said bounded contiguous locations.

10. The apparatus of claim 8 wherein said determining means includes:
    means for bounding all contiguous locations on said illuminated mining face identified as containing said mineral; and
    means for locating the center of mass of all said bounded contiguous locations.

11. The apparatus of claim 8 further comprising:
means for mechanically mining said illuminated mining face; and
means responsive to said determining means for guiding said mining means to mine on said mining face in a location about said determined centroid.

12. The apparatus of claim 1 further comprising:
means for mechanically mining said illuminated mining face; and
means responsive to said identifying means for guiding said mining means to mine on said mining face in a location about said determined centroid.

13. A method of automatically and dynamically identifying a vein of mineralization in a mine face comprising the steps of:
generating a broad spectrum beam of light, which beam of light is aimed at said mining face to illuminate said mining face;
producing, in response to said beam of light as returned from said illuminated mining face, with a camera an n * m pixel image, with each pixel being representative of a returned light level from a corresponding location on said illuminated mining face, where n and m are positive integers greater than 1;
interposing a selected one of a plurality of narrow bandwidth filters, each transmissive of only a predefined range of frequencies of light between said illuminated mining face and said camera to block the transmission of all of said returned light beam, except said narrow band of frequencies passed by said selected narrow bandwidth filter, from said illuminated mining face to said camera;
storing at least one mineral signature representative of the relative returned light level for a plurality of frequencies for a designated mineral;
comparing said returned light level for at least one of said n * m pixels for a plurality of images, produced by sequentially interposing each of a plurality of said narrow bandwidth filters between said illuminated mining face and said camera, with at least one of said stored mineral signatures; and
identifying, in response to said pixel for a predetermined number of said images being of illumination magnitude within a predetermined distance from said corresponding mineral signature value, the presence of said mineral in said mineral face at a location thereon corresponding to said pixel.

14. The method of claim 13, wherein each of said narrow bandwidth filters is transmissive of only a predefined range of frequencies of light which range is centered about a center frequency corresponding to one of said plurality of mineral signature frequencies, further comprising the step:
recording said plurality of images.

15. The method of claim 14 wherein said step of comparing sequentially compares all of said n * m pixels of all of said recorded images with said stored mineral signature to identify all the locations on said illuminated mining face containing said mineral.

16. The method of claim 14 wherein said step of comparing sequentially compares a predetermined subset of said n * m pixels of all of said recorded images with said stored mineral signature to identify all the locations on said illuminated mining face containing said mineral.

17. The method of claim 14 wherein said step of comparing includes:
dividing said n * m pixels into a plurality of contiguous subsets, each of which contain j * k pixels, where j and k are positive integers greater than zero;
generating an envelope representative of the maximum and minimum values of returned light for each subset for each image; and
sequentially comparing all of said subset envelopes of all of said recorded images with said stored mineral signature to identify all the locations on said illuminated mining face containing said mineral.

18. The method of claim 17 wherein said step of identifying identifies the presence of said mineral in said mineral face at a location thereon corresponding to said pixel subset when said corresponding stored mineral signature value representative of the relative returned light level for the corresponding frequency falls within said envelope.

19. The method of claim 13 further comprising the step of:
determining the centroid of said identified locations on said illuminated mining face containing said mineral.

20. The method of claim 19 wherein said step of determining includes:
bounding all contiguous locations on said illuminated mining face identified as containing said mineral; and
locating the centroid of said bounded contiguous locations.

21. The method of claim 19 wherein said step of determining includes:
bounding all contiguous locations on said illuminated mining face identified as containing said mineral; and
locating the center of mass of all said bounded contiguous locations.

22. The method of claim 19 further comprising the step of:
guiding an automated mining apparatus to mine on said mining face in a location about said determined centroid.

23. The method of claim 13 further comprising the step of:
guiding an automated mining apparatus to mine on said mining face in a location about said determined centroid.

24. An automatic vein follower for dynamically identifying a vein of mineralization in a mine face comprising:
means for generating a broad spectrum beam of light, which beam of light is aimed at said mining face to illuminate said mining face;
means aimed at said illuminated mining face and responsive to said beam of light as returned from said illuminated mining face, for producing an n * m pixel image, with each pixel being representative of a returned light level from a corresponding location on said illuminated mining face, where n and m are positive integers greater than 1;
means for storing at least one mineral signature representative of the relative returned light level for a plurality of frequencies for a designated mineral:
a plurality of narrow bandwidth filer means, each transmissive of only a predefined range of frequencies of light which range is centered about a center frequency corresponding to one of said plurality of mineral signature frequencies;

means for interposing a selected one of said narrow bandwidth filter means between said illuminated mining face and said producing means to block the transmission of all of said returned light beam, except said narrow band of frequencies passed by said selected narrow bandwidth filter means, from said illuminated mining face to said producing means;

means for comparing said returned light level for at least one of said n * m pixels for a plurality of images, produced by sequentially interposing each of a plurality of said narrow bandwidth filter means between said illuminated mining face and said producing means, with at least one of said stored mineral signatures;

means responsive to said pixel for a predetermined number of said images being of illumination magnitude within a predetermined distance from said corresponding mineral signature value for identifying the presence of said mineral in said mineral face at a location thereon corresponding to said pixel;

means for determining the centroid of said identified locations on said illuminated mining face containing said mineral;

means for mechanically mining said illuminated mining face; and means responsive to said identifying means for guiding said mining means to mine on said mining face in a location about said determined centroid.

* * * * *